(12) United States Patent
Ogura et al.

(10) Patent No.: US 8,106,133 B2
(45) Date of Patent: Jan. 31, 2012

(54) ELASTOMER MOLDING FOR ENDOSCOPE

(75) Inventors: Hitoshi Ogura, Higashiyamato (JP); Yuuri Takeuchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/838,884

(22) Filed: Jul. 19, 2010

(65) Prior Publication Data

US 2010/0280319 A1    Nov. 4, 2010

Related U.S. Application Data

(63) Continuation of application No. 12/333,503, filed on Dec. 12, 2008, now abandoned.

(30) Foreign Application Priority Data

Feb. 6, 2008   (JP) ................................. 2008-026669

(51) Int. Cl.
*C08G 63/00* (2006.01)

(52) U.S. Cl. .............. 525/444; 525/440.01; 525/440.02; 525/440.12; 525/448; 600/139

(58) Field of Classification Search ................... 525/444, 525/440.01, 440.02, 440.12, 448; 600/139
See application file for complete search history.

(56) References Cited

U.S. PATENT DOCUMENTS

| | | | |
|---|---|---|---|
| 3,193,522 A | 7/1965 | Fischer et al. | |
| 4,169,866 A | 10/1979 | von Bonin et al. | |
| 5,685,825 A | 11/1997 | Takase et al. | |
| 6,498,225 B2 | 12/2002 | Tebbe et al. | |
| 2006/0094858 A1* | 5/2006 | Turner et al. | 528/272 |
| 2008/0249213 A1 | 10/2008 | Park et al. | |

FOREIGN PATENT DOCUMENTS

| | | |
|---|---|---|
| EP | 0 294 179 A2 | 12/1988 |
| EP | 0 357 194 A1 | 3/1990 |
| EP | 1 867 471 A1 | 12/2007 |
| JP | 2001-346754 | 12/2001 |
| JP | 2002-153418 | 5/2002 |
| JP | 2004-141487 | 5/2004 |
| JP | 2007-65587 | 3/2007 |
| WO | WO 2006/095970 A1 | 9/2006 |

OTHER PUBLICATIONS

Pankratov, V. A., Russian Chemical Reviews, 62 (12) 1119-1138, 1993.

Olabisi, O., Handbook of Thermoplastics, Marcel Dekker, Inc., 1997, p. 397-399, 404-405, 413.

* cited by examiner

*Primary Examiner* — David W Wu
*Assistant Examiner* — Robert Jones, Jr.
(74) *Attorney, Agent, or Firm* — Scully, Scott, Murphy & Presser, P.C.

(57) ABSTRACT

The invention provides a flexible tube for an endoscope, which is excellent in elasticity (impact resilience), has suitable flexibility and also has chemical resistance. Disclosed is a flexible tube for an endoscope including a flexible-tube material covered thereon with a jacket, wherein the jacket contains two or more thermoplastic polyester elastomers crosslinked therein.

17 Claims, 1 Drawing Sheet

ELASTOMER MOLDING FOR ENDOSCOPE

CROSS-REFERENCE TO RELATED APPLICATIONS

This application is a continuation application of U.S. Ser. No. 12/333,503, filed on Dec. 12, 2008, which is based upon and claims the benefit of priority from prior Japanese Patent Application No. 2008-026669, filed Feb. 6, 2008, the entire contents of which are incorporated herein by reference.

BACKGROUND OF THE INVENTION

1. Field of the Invention

The present invention relates to an elastomer molding and in particular to an elastomer molding as a flexible tube for an endoscope.

2. Description of the Related Art

In an endoscope, a flexible elastomer molding is used as a jacket for flexible Lube. Because an endoscope is repeatedly used and should be cleansed and sterilized every time it is used, the jacket for a flexible tube should be impermeable to body fluids, cleaning liquids, antiseptic solutions etc. The jacket for a flexible tube should have such suitable flexibility and elasticity as not to impair insertion into the body cavity.

The conventional jacket for an endoscopic flexible tube has been formed from a mixed resin of a thermoplastic polyester elastomer (TPC) and a thermoplastic polyurethane elastomer (TPU) or a mixed resin of TPU and TPC compounded with soft polyvinyl chloride (PVC).

With recent diversification of sterilization techniques, thermal resistance is also required of the endoscope. However, TPU is inferior to TPC in thermal resistance, and thus TPU is not suitable for use where thermal resistance is required, and TPC is preferably used.

This TPC is composed of a crystallized hard segment functioning as a crosslinking site and an uncrystallized soft segment exhibiting flexibility. TPC comprising polybutylene naphthalate (PBN) as a hard segment is particularly excellent in chemical resistance and also shows autoclave resistance (see, for example, JP-A 2004-141487 [KOKAI]). However, this TPC comprising PBN as a hard segment is rigid with low flexibility attributable to its chemical structure and is thus not suitable for use in the tip of a long endoscope for the large intestine.

On the other hand, TPC comprising polybutylene terephthalate (PBT) as a hard segment has sufficient flexibility for use in the tip of an endoscope. However, TPC comprising PBT has a problem that it is inferior in chemical resistance to TPC comprising PBN and is lacking autoclave resistance.

BRIEF SUMMARY OF THE INVENTION

An object of the present invention is to provide a flexible tube for an endoscope, which is excellent in elasticity (impact resilience), has suitable flexibility and also has chemical resistance.

For regulating flexibility and for improving chemical resistance, the inventors have melt-mixed a thermoplastic polyester elastomer (TPC) comprising PBN as a hard segment, with TPC comprising PBT. However, these two TPCs are not completely compatible with each other because of the difference in their segments. Accordingly, the resulting mixture showed significant deterioration in elasticity and could not be satisfactory in resistance to various chemical solutions, for use as a jacket of a flexible tube for an endoscope. Hence, the inventors made extensive study, and as a result, they found that crosslinking of two or more TPCs is effective, and the present invention was thereby completed.

That is, the present invention provides an elastomer molding for an endoscope, which comprises two or more thermoplastic polyester elastomers crosslinked therein.

According to a preferable embodiment of the invention, the two or more thermoplastic polyester elastomers are crosslinked using a carbodiimide compound as a crosslinking agent. According to another preferable embodiment of the invention, the average molecular weight of the carbodiimide is 10000 or more. According to another embodiment of the invention, the hard segment of at least one of the thermoplastic polyester elastomers is polybutylene terephthalate. According to another embodiment of the invention, the jacket further contains 5 to 25 parts by weight of plasticizer.

According to another embodiment of the invention, there is also provided the elastomer molding for an endoscope, which is formed as a jacket for covering the surface of a flexible tube for an endoscope. According to still another embodiment of the invention, there is provided a flexible tube for an endoscope, which is covered with a jacket made of the elastomer molding described above.

As described above, TPC comprising PBN is low in flexibility (rigid). Thus, when TPCs comprising PBN are crosslinked with each other, the product is made lower in flexibility. Accordingly, at least one of TPCs is preferably one comprising PBT as a hard segment.

TPC can be crosslinked by various methods. A method of comprising a carbodiimide compound is particularly effective because the compound can also functions as a hydrolysis-resistant agent. The carbodiimide used is less liable to exhibit blooming as the molecular weight increases, thus reducing its eluted amount. Accordingly, the carbodiimide compound can be preferably used when the elastomer molding is used for medical purposes. When the flexibility of the elastomer molding is to be further increased (softened), a plasticizer may be added. The elastomer molding according to the present invention has TPC molecules chemically bound to one another and is thus less liable to exhibit plasticizer bleeding than a simple mixture of non-crosslinked TPCs.

The thus constituted elastomer molding of the present invention and an endoscopic flexible tube using the same are excellent in elasticity (impact resilience) and have appropriate flexibility because two kinds of thermoplastic elastomers are crosslinked with each other. Accordingly, they have an excellent distinctive feature of excellent insertability to relieve the pain (burden) of a patient. The elastomer molding of the present invention and an endoscopic flexible tube using the same are not only resistant to various cleaning liquids, antiseptic solutions and low-temperature plasma sterilization but are also excellent in hydrolysis resistance. Therefore, they can be autoclaved (sterilization with steam under high pressure) which is useful in prevention of infection, and can maintain high insertability over a long period.

DETAILED DESCRIPTION OF THE INVENTION

Figure 1:
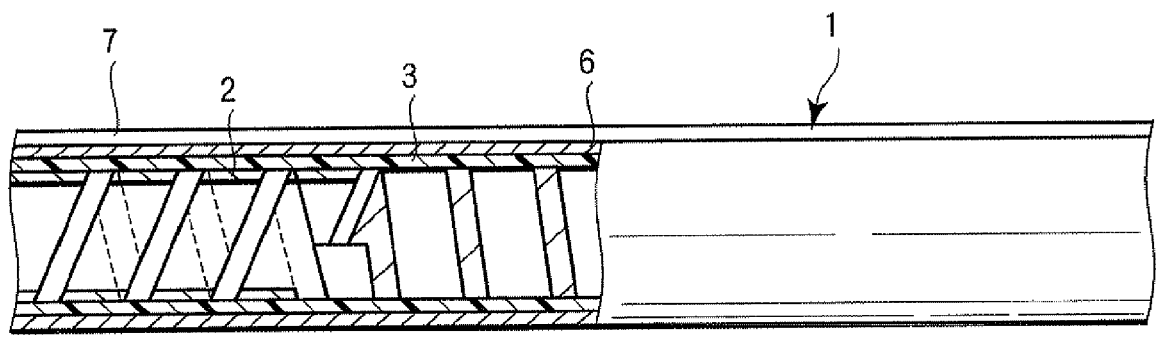
FIG. 1 is a sectional view of a flexible tube for an endoscope according to one embodiment of the present invention.
Figure 2:
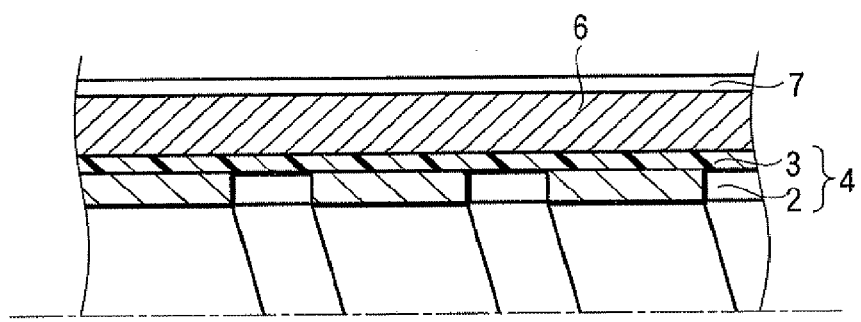
FIG. 2 is an enlarged view of a part of the flexible tube in FIG. 1.

Hereinafter, embodiments of the invention will be described in detail with reference to the drawings. FIG. 1 shows an endoscopic flexible tube 1 in one embodiment of the present invention. FIG. 2 is an enlarged view of a part of the endoscopic flexible tube shown in FIG. 1. As shown in the figure, the endoscopic flexible tube (hereinafter referred to as a "flexible tube") 1 is composed of a flexible-tube material 4 and a jacket 6 for covering the periphery thereof. The flexible-tube material 4 is composed of a spiral tube 2 and a mesh tube 3 for covering the periphery thereof. The jacket 6 is further coated with a coating layer 7.

As the material constituting the spiral tube 2, stainless steel or a copper alloy can be used. The mesh tube 3 is constituted by braiding a plurality of metallic or nonmetallic thin lines. Stainless steel and synthetic resin can be used as materials of metallic and nonmetallic thin lines, respectively. For improving adhesion to the jacket, a mixture of metallic and nonmetallic thin lines is braided in some cases.

The jacket 6 for covering the periphery of the flexible-tube material 4 is composed of a resin having two or more TPCs crosslinked therein. TPCs used in this resin may be various ones known in the art, and include, for example, Hytrel (manufactured by Du Pont-Toray Co., Ltd.), Grilux (Dainippon Ink And Chemicals, Incorporated), Primalloy (manufactured by Mitsubishi Chemical Corporation), Arnitel (manufactured by DSM), and Pelprene (manufactured by Toyobo Co., Ltd.).

Crosslinking of TPCs may be conducted by any method such as a method of heating in the presence of a crosslinking agent and a method of irradiation with ionizing radiation such as γ-rays or an electron beam. A preferably used crosslinking agent includes, but is not limited to, carbodiimide compounds. Also, conventionally known crosslinking agents normally used in crosslinking of elastomers such as epoxylated thermoplastic elastomers can be used singly or as a combination thereof.

Many thermoplastic elastomers will, when crosslinked, lose thermoplasticity. However, their thermoplasticity can be maintained by appropriately regulating the degree of crosslinkage. When a carbodiimide compound is used as the crosslinking agent, 0.5 to 5 parts by weight of the carbodiimide compound is preferably added to TPCs.

For regulating flexibility, a plasticizer may be added to TPCs. The plasticizer can be added in an amount of 5 to 25 parts by weight although its amount is not limited thereto. As the plasticizer, those known in the art, which are based on fatty ester, glycol, glycerin, epoxy and polyester, may be used singly or as a combination thereof.

Also, TPCs may be compounded if necessary with fillers. The fillers that can be used include, but are not limited to, inorganic fillers selected from the group consisting of carbon black, silica, barium sulfate, titanium oxide, aluminum oxide, calcium carbonate, calcium silicate, magnesium silicate and aluminum silicate, organic fillers selected from the group consisting of polytetrafluoroethylene resin, polyethylene resin, polypropylene resin, phenol resin, polyimide resin, melamine resin and silicone resin, and arbitrary combinations thereof.

Also, TPCs may optionally be compounded with fibers. The fibers include, but are not limited to, inorganic fibers selected from the group consisting of glass fibers, alumina fibers and rock wool, organic fibers selected from the group consisting of cotton, wool, silk, hemp, nylon fibers, aramid fibers, vinylon fibers, polyester fibers, rayon fibers, acetate fibers, phenol-formaldehyde fibers, polyphenylene sulfide fibers, acrylic fibers, polyvinyl chloride fibers, polyvinylidene chloride fibers, polyurethane fibers and tetrafluoroethylene fibers, and arbitrary combinations thereof.

Lubricants, stabilizers, weathering stabilizers, ultraviolet absorbers and antistatic agents can also be added in such a range that the effect of the present invention is not degraded.

The TPC of the present invention can be produced by a variety of conventional methods. Generally, melt-kneading is carried out with a kneading machine such as a kneader, a Banbury mixer or a continuous kneading extruder. The kneading temperature may be an arbitrary temperature as long as it is a temperature at which the respective components are uniformly dispersed and which is below the decomposition temperature of TPC and additives.

When TPCs are crosslinked by irradiation with ionizing radiations, a co-crosslinking agent is added to two or more TPCs which are then kneaded by the method described above. Then, the product can be formed into a flexible tube and irradiated with ionizing radiations.

EXAMPLES

Hereinafter, the present invention will be described in more detail with reference to the Examples.

<Examples>

According to the formulation shown in Table 1, two TPCs, a crosslinking agent, and, optionally, a plasticizer were blended and kneaded by a continuous kneading extruder to yield an elastomer molding. The periphery of a core material consisting of a spiral tube covered with a mesh tube was covered with the resulting elastomer molding to produce the flexible tube for an endoscope in each of Examples 1 to 6.

Comparative Examples

According to the formulations shown in Table 1, the flexible tubes for an endoscope in Comparative Examples 1 to 4 were prepared in the same manner as in the Examples above except that no crosslinking agent was added. In Comparative Example 1, however, the flexible tube was produced by using TPU as it is.

TABLE 1

| Formulation Table (unit: parts by weight) | | | | | | | | | | | |
|---|---|---|---|---|---|---|---|---|---|---|---|
| | | Examples | | | | | | Comparative Examples | | | |
| | | 1 | 2 | 3 | 4 | 5 | 6 | 1 | 2 | 3 | 4 |
| Elastomers | PBN-based TPC-ET A | 50 | — | — | 75 | — | — | — | 50 | 75 | — |
| | PBN-based TPC-ET B | — | — | — | 25 | — | — | — | — | 25 | — |
| | PBT-based TPC-ET C | 50 | 50 | 50 | — | — | — | — | 50 | — | — |
| | PBT-based TPC-ET D | — | 50 | — | — | — | — | — | — | — | — |
| | PBT-based TPC-ET E | — | — | 50 | — | — | — | — | — | — | — |
| | PBT-based TPC-ET F | — | — | — | — | 80 | 80 | — | — | — | 80 |

TABLE 1-continued

Formulation Table (unit: parts by weight)

|  |  | Examples | | | | | | Comparative Examples | | | |
|---|---|---|---|---|---|---|---|---|---|---|---|
|  |  | 1 | 2 | 3 | 4 | 5 | 6 | 1 | 2 | 3 | 4 |
|  | PBT-based TPC-ET G | — | — | — | — | 20 | 20 | — | — | — | 20 |
|  | TPU H | — | — | — | — | — | — | 100 | — | — | — |
| Crosslinking agents | Carbodiimide Compound I (average molecular weight; 15000 g/mol) | 2 | 2 | — | 2 | — | — | — | — | — | — |
|  | Carbodiimide Compound J (average molecular weight: 3000 g/mol) | — | — | 2 | — | 2 | 1 | — | — | — | — |
| Plasticizer | Epoxylated Soybean Oil K | — | — | — | — | 15 | 10 | — | — | — | 15 |

PBT: Polybutylene terephthalate
PBN: Polybutylene naphthalate
TPC-ET: TPC with polyether as soft segment
TPU: Polyurethane elastomer The flexible tubes in Examples 1 to 6 and Comparative Examples 1 to 4 were examined for their flexibility, elasticity, thermal resistance and chemical resistance. In a thermal resistance test, the sample was heated to 136° C. for 100 hours and then its molten state was visually judged. In a chemical resistance test, the sample was left in 3.7% aqueous peracetic acid at 53° C. for 30 days, and then its outward appearance was visually judged. The test results are shown in Table 2. The meanings of the symbols in test results are as follows: ⊚, very good; ○, good; Δ, acceptable; and X, unacceptable.

TABLE 2

Test results

| | Flexibility | Elasticity | Thermal resistance | Chemical resistance | Special affairs |
|---|---|---|---|---|---|
| Example 1 | Δ | ○ | ⊚ | ○ | Superior to Comparative Example 2 in elasticity |
| Example 2 | ○ | ○ | ⊚ | Δ | |
| Example 3 | ○ | ○ | ⊚ | Δ | |
| Example 4 | Δ | ○ | ⊚ | ⊚ | Superior to Comparative Example 3 in elasticity |
| Example 5 | ⊚ | ○ | Δ | Δ | |
| Example 6 | ⊚ | ○ | ○ | Δ | Superior to Comparative Example 4 in elasticity, thermal resistance and chemical resistance No plasticizer bleeding |
| Comparative Example 1 | ⊚ | ⊚ | X | X | |
| Comparative Example 2 | Δ | Δ | ⊚ | ○ | |
| Comparative Example 3 | Δ | X | ⊚ | ⊚ | |
| Comparative Example 4 | ⊚ | Δ | Δ | X | Plasticizer bleeding |

As can be seen from Table 2, Example 1 and Comparative Example 2 are the same in elastomer composition, but Example 1 where a crosslinking agent is contained is superior to Comparative Example 2 in elasticity. Example 4 where a crosslinking agent is contained is superior to Comparative Example 3 in elasticity. Example 6 is superior to Comparative Example 4 in elasticity, thermal resistance and chemical resistance, and plasticizer bleeding did not occur. In Comparative Example 4, on the other hand, plasticizer bleeding occurred.

As is evident from these test results, Examples 1 to 6 showed results generally excellent in flexibility, elasticity, thermal resistance and chemical resistance. It was found that the elastomer molding having two TPCs crosslinked therein has characteristics superior to those of a mixture having two TPCs simply mixed therein. It was also demonstrated that plasticizer bleeding is suppressed by crosslinking TPCs.

As described above, according to the present invention, an elastomer molding for an endoscope, which is excellent in elasticity (impact resilience), has suitable flexibility and also has thermal resistance and chemical resistance is obtained.

The invention is not limited to the examples described above, and can be practiced with various modifications without departure from the gist of the invention.

(Additional Notes)

Additional Note 1: A flexible tube for an endoscope comprising a flexible tube covered thereon with a jacket, wherein the jacket comprises two or more thermoplastic polyester elastomers crosslinked therein.

Additional Note 2: The flexible tube for an endoscope as mentioned above, wherein the two or more thermoplastic polyester elastomers are crosslinked using a carbodiimide compound as a crosslinking agent.

Additional Note 3: The flexible tube for an endoscope as mentioned above, wherein an average-molecular weight of the carbodiimide is 10000 or more.

Additional Note 4: The flexible tube for an endoscope as mentioned above, wherein a hard segment of at least one of the thermoplastic polyester elastomers is polybutylene terephthalate.

Additional Note 5: The flexible tube for an endoscope as mentioned above, wherein the jacket further comprises 5 to 25 parts by weight of a plasticizer.

Additional Note 6: A flexible-tube jacket for an endoscope, which comprises two or more thermoplastic polyester elastomers crosslinked therein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An elastomer molding comprising a first thermoplastic polyester elastomer comprising a hard segment composed of polybutylene terephthalate, a second thermoplastic polyester elastomer comprising a hard segment composed of polybutylene naphthalate, and a carbodiimide compound as a crosslinking agent, wherein the first thermoplastic polyester elastomer is crosslinked with the second thermoplastic polyester elastomer, and the elastomer molding further comprises a plasticizer.

2. The elastomer molding according to claim 1, wherein an average molecular weight of the carbodiimide compound is 3000 or more.

3. The elastomer molding according to claim 1, wherein an average molecular weight of the carbodiimide compound is 10000 or more.

4. The elastomer molding according to claim 1, wherein an average molecular weight of the carbodiimide compound is 15000 or more.

5. The elastomer molding according to claim 1, wherein plasticizer is a compound selected from the group consisting of fatty ester, glycol, glycerin, epoxy and polyester, or a combination thereof.

6. The elastomer molding according to claim 1, wherein the plasticizer is selected from epoxy compound.

7. A jacket for covering the surface of a flexible tube for an endoscope, wherein the jacket is made of the elastomer molding as defined in claim 1.

8. The jacket according to claim 7, wherein an average molecular weight of the carbodiimide compound is 3000 or more.

9. The jacket according to claim 7, wherein an average molecular weight of the carbodiimide compound is 10000 or more.

10. The jacket according to claim 7, wherein an average molecular weight of the carbodiimide compound is 15000 or more.

11. The jacket according to claim 7, wherein the plasticizer is a compound selected from the group consisting of fatty ester, glycol, glycerin, epoxy and polyester, or a combination thereof.

12. The jacket according to claim 7, wherein the plasticizer is selected from epoxy compound.

13. A flexible tube for an endoscope, which is covered with a jacket, wherein the jacket is made of the elastomer molding as defined in claim 1.

14. The flexible tube according to claim 13, wherein an average molecular weight of the carbodiimide compound is 3000 or more.

15. The flexible tube according to claim 13, wherein an average molecular weight of the carbodiimide compound is 10000 or more.

16. The flexible tube according to claim 13, wherein an average molecular weight of the carbodiimide compound is 15000 or more.

17. The flexible tube according to claim 13, wherein the plasticizer is a compound selected from the group consisting of fatty ester, glycol, glycerin, epoxy and polyester, or a combination thereof.

* * * * *